US010556130B2

(12) United States Patent
Dolney et al.

(10) Patent No.: US 10,556,130 B2
(45) Date of Patent: Feb. 11, 2020

(54) WATER-EQUIVALENT TWO-DIMENSIONAL DETECTOR METHODS, SYSTEMS AND APPARATUS FOR PROTON THERAPY

(71) Applicant: The Trustees of the University of Pennsylvania, Philadelphia, PA (US)

(72) Inventors: Derek Dolney, Huntingdon Valley, PA (US); Robert Hollebeek, Berwyn, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 142 days.

(21) Appl. No.: 15/324,334

(22) PCT Filed: Jul. 8, 2015

(86) PCT No.: PCT/US2015/039511
§ 371 (c)(1),
(2) Date: Jan. 6, 2017

(87) PCT Pub. No.: WO2016/007599
PCT Pub. Date: Jan. 14, 2016

(65) Prior Publication Data
US 2017/0203127 A1    Jul. 20, 2017

Related U.S. Application Data

(60) Provisional application No. 62/021,935, filed on Jul. 8, 2014.

(51) Int. Cl.
*A61N 5/10*    (2006.01)

(52) U.S. Cl.
CPC ......... *A61N 5/1075* (2013.01); *A61N 5/1071* (2013.01); *A61N 2005/1076* (2013.01); *A61N 2005/1087* (2013.01)

(58) Field of Classification Search
CPC ................ A61N 5/1071; A61N 5/1075; A61N 2005/1076; A61N 2005/1087
See application file for complete search history.

(56) References Cited

U.S. PATENT DOCUMENTS

| 2002/0080912 | A1 | 6/2002 | Mackie |
| 2012/0104270 | A1 | 5/2012 | Marchand |
| 2012/0261585 | A1 | 10/2012 | De Oliveira |
| 2012/0273665 | A1 | 11/2012 | Schulte |

OTHER PUBLICATIONS

International Preliminary Report on Patentability fro International Application No. PCT/EP2015/039511, dated Oct. 7, 2015, 5 pages.
International Search Report and Written Opinion of the International Searching Authority for International Application No. PCT/US2015/039511, dated Oct. 7, 2015, 6 pages.

*Primary Examiner* — Carrie R Dorna
(74) *Attorney, Agent, or Firm* — BakerHostetler

(57) ABSTRACT

A particle detection system for calibrating a particle therapy machine or validating a particle therapy plan. The detector system includes one or more two-dimensional particle detection layers for receiving a particle beam and one or more compensating layers. The compensating layer(s) are configured to adjust energy loss and scatter values introduced by the one or more two-dimensional particle detection layers to match water-equivalent values. Each compensation layer is positioned adjacent a respective one of the one or more two-dimensional particle detection layers.

18 Claims, 12 Drawing Sheets

WATER-EQUIVALENT TWO-DIMENSIONAL DETECTOR METHODS, SYSTEMS AND APPARATUS FOR PROTON THERAPY

CROSS-REFERENCE TO RELATED APPLICATIONS

This application is a National Phase application of International Application No. PCT/US2015/039511, filed Jul. 8, 2015 entitled "WATER-EQUIVALENT TWO-DIMENSIONAL DETECTOR METHODS, SYSTEMS, AND APPARATUS FOR PROTON THERAPY" which claims priority to U.S. Provisional Application No. 62/021,935 titled "WATER EQUIVALENT TWO-DIMENSIONAL DETECTOR METHODS, SYSTEMS, AND APPARATUS FOR PROTON THERAPY," filed on Jul. 8, 2014, the contents of which are incorporated by reference herein.

STATEMENT REGARDING FEDERALLY SPONSORED RESEARCH

This invention was made with government support under Contract Agreement No. DAMD17-W81XWH-04-2-0022 awarded by the US Army Medical Research and Material Command. The Government has certain rights in this invention.

BACKGROUND OF THE INVENTION

Radiation therapy, such as proton radiation therapy, is starting to become widely adopted for cancer treatment due to its capability to produce maximum radiation dosage in a small area at a controlled depth in the body of a patient. Particle machines used for such treatment require calibration prior to use. There exists a need for improved detector systems for use with calibration and verification of particle machines used in radiation therapy.

SUMMARY OF THE INVENTION

Aspects of the invention include particle detection systems for calibrating a particle therapy machine or validating a particle therapy plan. The detector system includes one or more two-dimensional particle detection layers for receiving a particle beam and one or more compensating layers. The compensating layer(s) are configured to adjust energy loss and scatter values introduced by the one or more two-dimensional particle detection layers to match water-equivalent values. Each compensation layer is positioned adjacent a respective one of the one or more two-dimensional particle detection layers.

Further aspects of the invention include methods for identifying a compensation layer material for use in a particle detection system. The methods include—computing an energy loss and scatter values given the material and dimension of one or more detector layers in the particle detection system, generating values for a density, atomic number, and thickness of the compensating layer that in combination with the detector layers yield a water equivalent system, and identifying an available material satisfying a combination of density, atomic number, and thickness.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. Included in the drawings are the following figures.

DETAILED DESCRIPTION OF THE INVENTION

Beams of protons, pions, or heavier charged particles (such as carbon ions) are or have been used to treat tumors inside the human body because of the precision with which they can reach their target and deposit most of their energy with minimal exit dose and scatter. It is ideal that the beam energy and modulation be accurately controlled so that the beam reaches only its intended target. Therefore, quality assurance (QA) measurements need to be made at various points along the beam longitudinally. However, beams get distorted/perturbed as they pass through a detector array and an accurate quality measurement requires placing a detector at various points and generating the beam multiple times for each measurement. By adding a compensating layer of material downstream of a two dimensional detector, the beam suffers a net distortion from the detector and compensating layer similar to how it would suffer in water (or a water-approximate material, or any reference material) of the same physical thickness. The reference energy loss and scatter values will typically be water since that is the standard reference medium for dosimetric calibrations in radiation therapy. The addition of a compensating layer provides controllability to the distortion suffered by the beam and thus multiple detector arrays can be placed in one instance of measurement along the beam path while achieving water equivalent distortions at each point.

Figure 1:
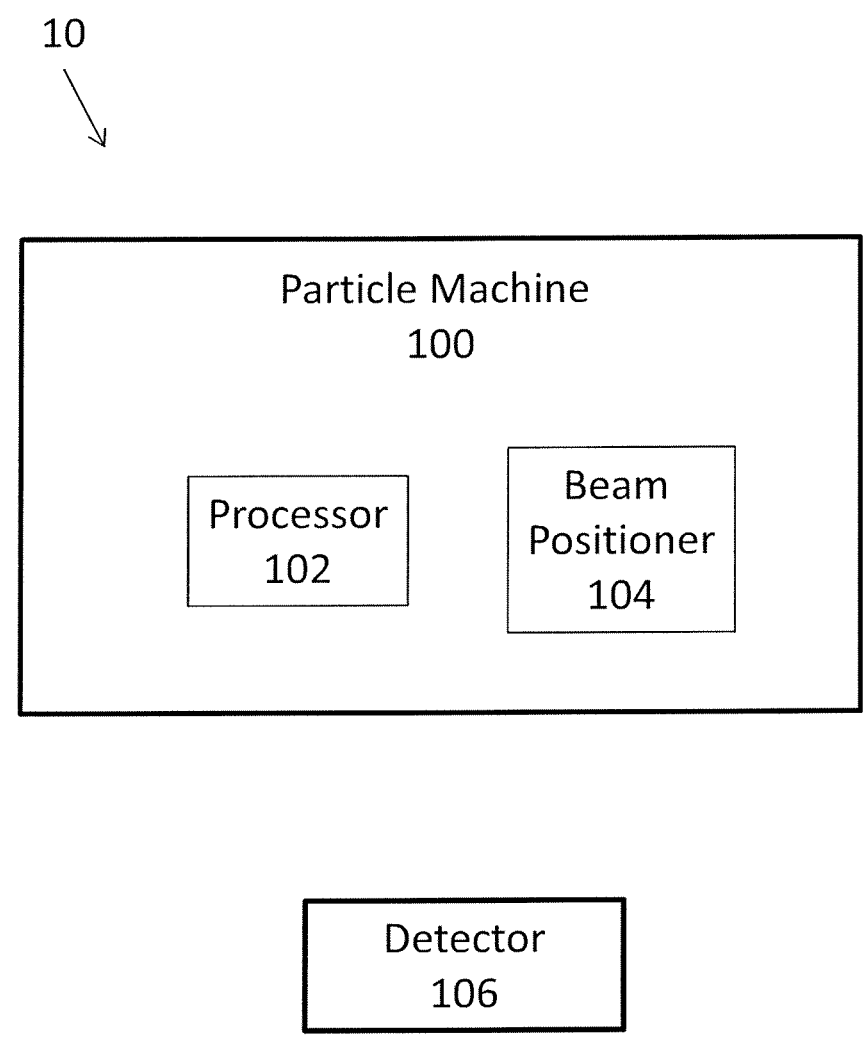
FIG. 1 is a functional block diagram of a particle beam system according to aspects of the invention.

Referring to FIG. 1, a functional diagram of a particle detection system 10 in accordance with aspects of the invention is depicted. The system 10 includes a particle machine 100 and a detector 106. The particle machine 100 includes a processor 102 and a beam positioner 104. The particle machine 100 may be configured for emission of beams of charged particles (e.g., electrons, pions, protons, carbon ions, etc.) and/or uncharged particles (e.g., photons, i.e X-rays, gamma rays, etc.), produced by any type of particle accelerator (e.g., cyclotron, synchrotron, etc.) and possibly employing a target to generate secondary particles. The above listed charged particles, uncharged particles, and particle accelerators is exemplary and not exclusive. One of skill in the art will understand other suitable particles and/or particle accelerators from the disclosure herein. In an embodiment, the particle machine 100 is configured for emission of protons. The processor 102 controls the operations of the particle machine 100 such that adjustments can be made by a user of the particle machine 100 (e.g., intensity of the beam, position of the beam, energy of the beam, etc.) via the beam positioner 104 in accordance with measurements taken during, for example, calibration. The system 10 also includes as detector 106 configured to detect the beam emitted from the particle machine 100. The detector 106 may be a parallel plate detector, a Micromegas detector, GEM detector, other micro-pattern gaseous detectors, a silicon detector, a detector employing gas-based, liquid-based, or solid-based scintillator material, etc., and may include multiple layers of detectors (e.g., dual-layer detectors with readout strips mounted orthogonally, etc). Particular functionalities and examples of particle detection systems, such as system 10, are disclosed below.

Figure 2:
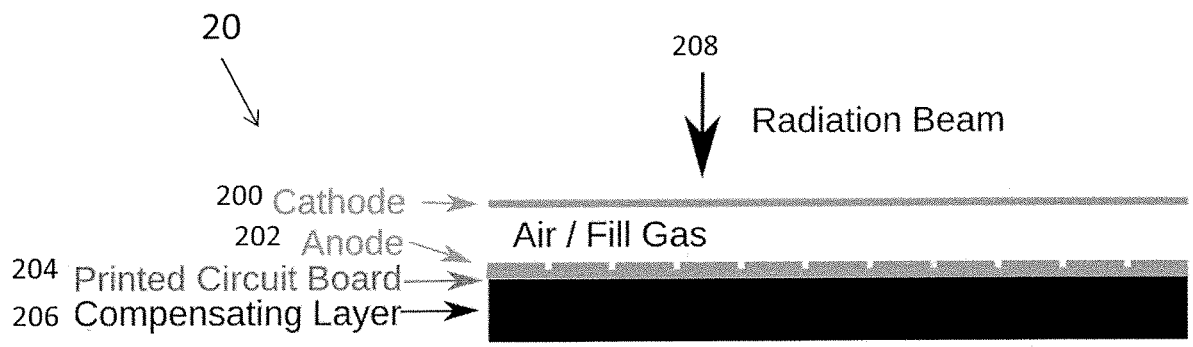
FIG. 2 is a cross-sectional diagram of a detector system in accordance with aspects of the invention.

FIG. 2 is a cross-sectional diagram of a detector assembly according to aspects of the invention. The detector assembly 20 includes a cathode 200, an anode 202, a printed circuit board (PCB) 204, and a compensating layer 206. Disposed between the cathode 200 and the anode 202 is gas to fill the space between the cathode 200 and the anode 202. The detector assembly 20 is configured to receive a radiation beam 208 (e.g., particle beam, proton beam, etc.) at the cathode 200, which then passes to the PCB 204 that is constructed to detect the properties of the beam 208. As the beam 208 passes through the cathode 200, fill gas, and anode 202 to the PCB 204, the beam suffers distortion (e.g., diffraction, back-scatter, energy loss, Coulomb scattering, etc.). Thus, the compensating layer 206 is positioned below the PCB 204 to compensate for the distortion as the beam 208 passes through the PCB 204 and through the compensating layer 206. In an embodiment, the compensating layer 206 is graphite-based. For example, high-purity graphite for high-density layers are used. Graphite-based layers are not strictly required and other suitable materials exist: boron carbide has an atomic number similar to graphite but even higher density; polymers such as A-150 tissue equivalent plastic, acrylic, or plexiglass; oxides such as beryllium oxide or aluminum oxide have higher density and so could be thinner at the cost of somewhat higher Z (so would be appropriate to compensate a lower Z detector or in case the scattering compensation performance is to sacrificed for thinness); metals such as titanium, zinc, or iron have the highest density but also very high Z so are likely only appropriate for detectors making use of low density, low Z materials such as some exotic detector filled with hydrogen gas. The choice of material may be dictated by, for example cost, availability, mechanical stability, or radiation tolerance, as will be understood by those of skill in the art from the description herein. For some detectors and applications it is even possible that multiple layers of distinct materials may be used to achieve acceptable total density and atomic number while balancing the other practical considerations mentioned.

Figure 3:
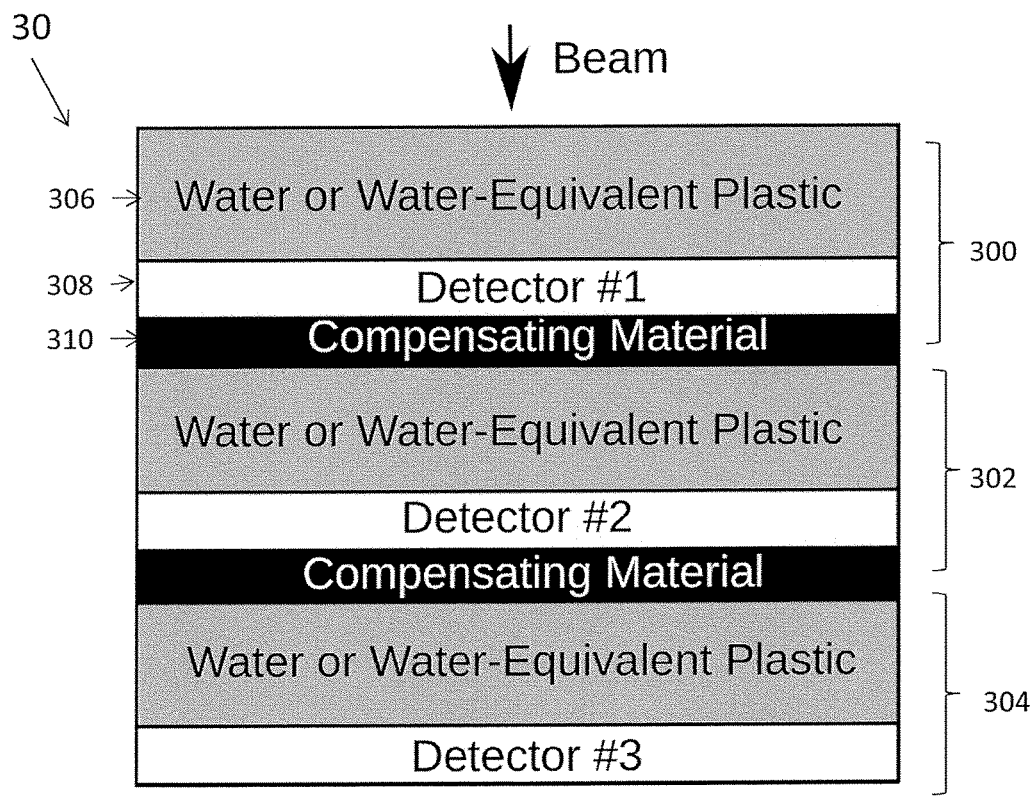
FIG. 3 is a diagram of a detector system according to aspects of the invention.
Figure 4:
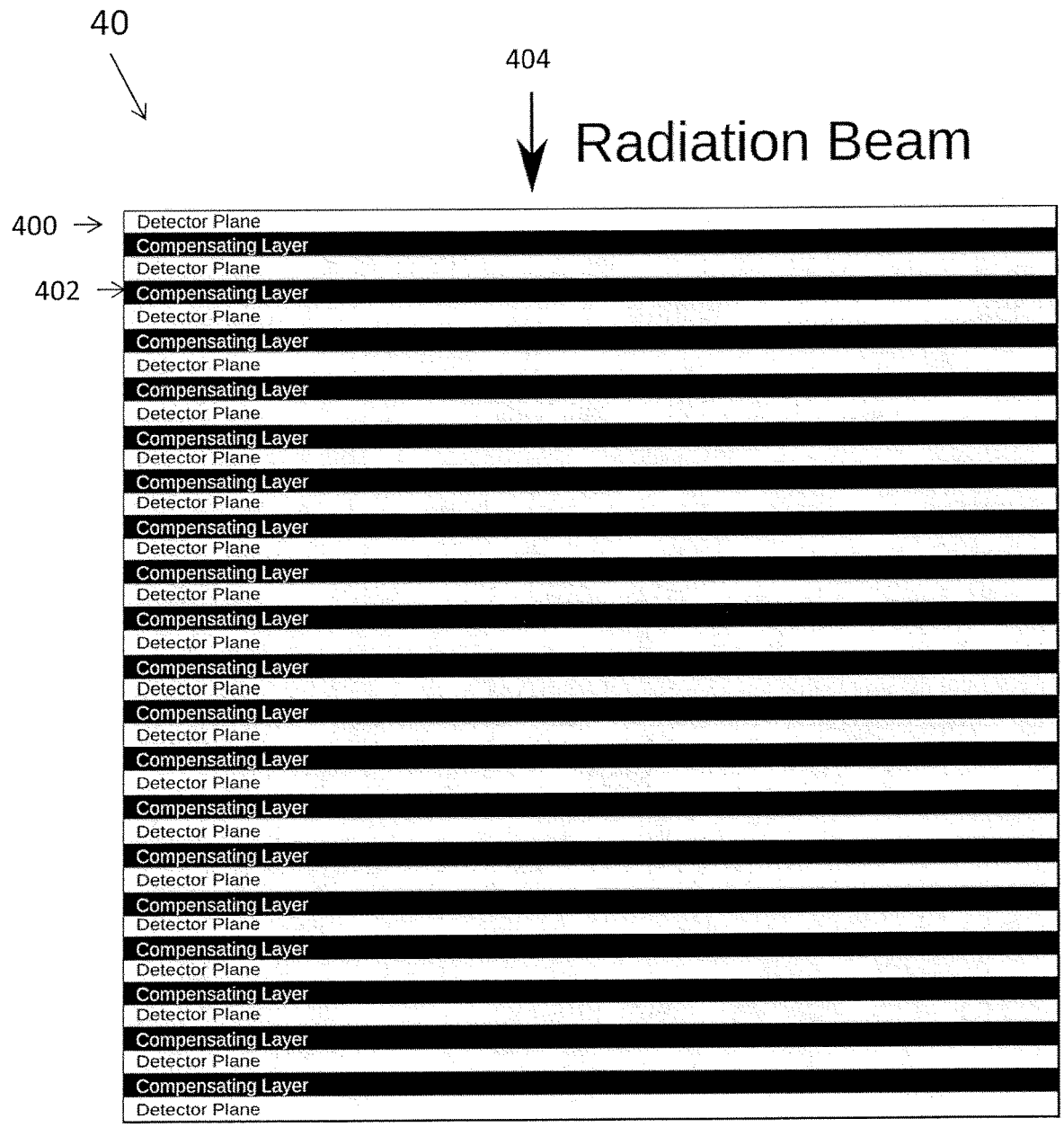
FIG. 4 is a diagram of a detector system in accordance with aspects of the invention.

Since the compensating layer compensates for the distortion of a beam resulting from the beam passing through the detector assembly, multiple detector assemblies with the compensating layers can be aligned, stacked and utilized in conjunction. For example, FIG. 3 depicts a detector assembly 30 with three detector layers 300, 302, and 304. Each layer includes a layer of water or water equivalent plastic 306 (such as Gammex 457 or equivalent), a detector plane 308, and a compensating layer 310 constructed of compensating material disposed below each detector plane. It is contemplated that multiple detector layers beyond three can be used, as is depicted in the assembly of FIG. 4. Between each detector plane 400 in the assembly 40 is a compensating layer 402 to compensate for distortion of the radiation beam 404 as it passes through the detector assembly 40.

Figure 5:
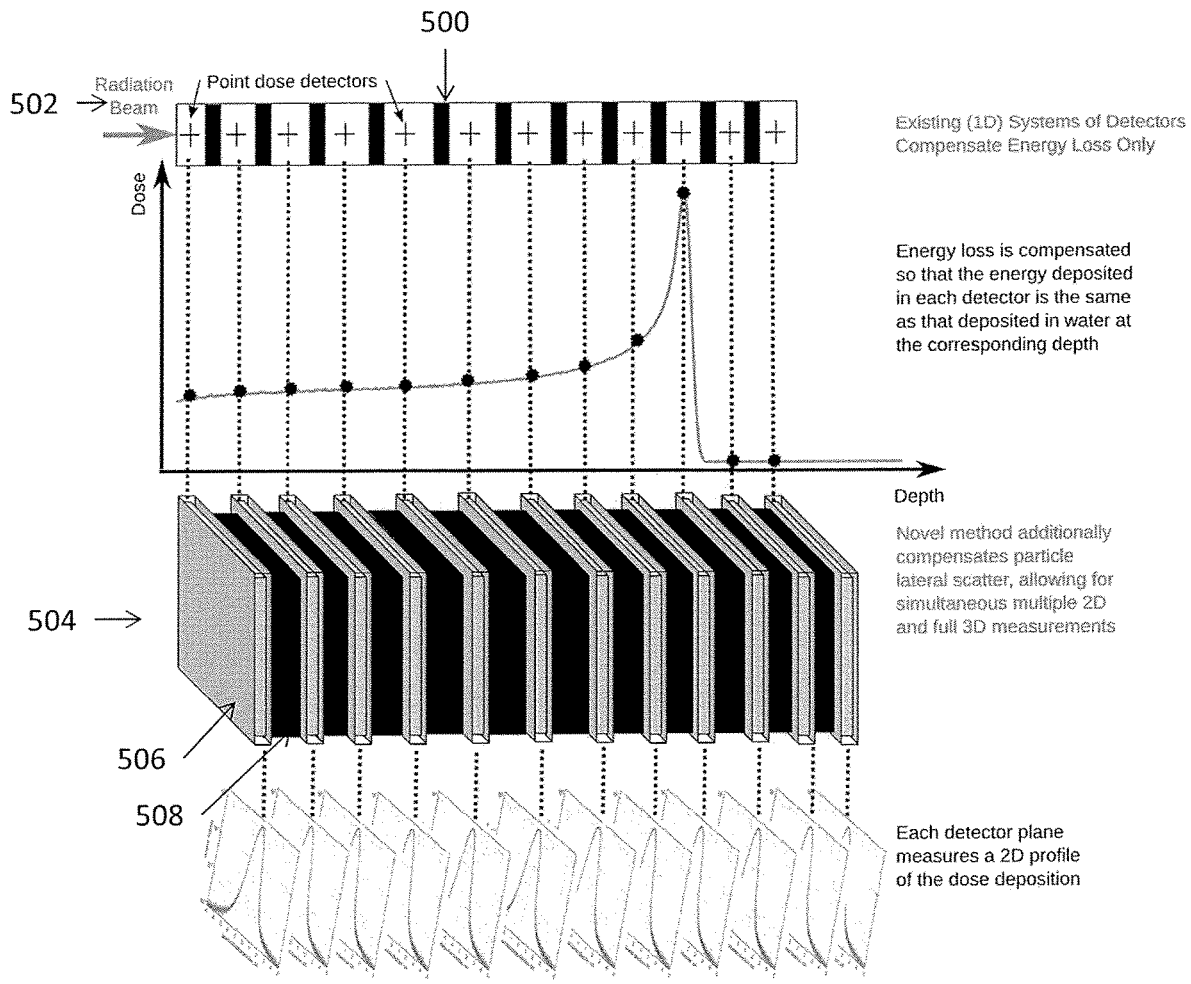
FIG. 5 is a comparative diagram between a one dimensional detector system and a two dimensional detector system.

Existing one dimensional systems of detectors compensate for energy loss of a particle beam only. The detector assemblies disclosed herein allow for compensation of both energy loss and lateral scatter across multiple two dimensional detector assemblies, allowing for simultaneous two dimensional measurements and full three dimensional measurements. Referring next to FIG. 5, a comparative diagram of a one dimensional detector system and a two dimensional detector system is shown. As shown, the one dimensional detector system 500 only detects energy loss, and not scatter of the radiation beam 502. The two dimensional detector system 504 can detect lateral scatter of the radiation beam system 502 caused by the radiation beam 502 passing through each detector 506 of the detector system 504. The addition of a compensation layer 508 between each detector 506 of the two dimensional detector system 504 permits compensation for both energy loss and lateral scatter of the radiation beam 502 as it passes through each detector 506. Thus, a two dimensional plane profile can be measured at each detector 506, and the combination of the plane profiles allows for a full three dimensional measurement of the radiation beam 502 through the depth of the detector system 504.

Figure 6:
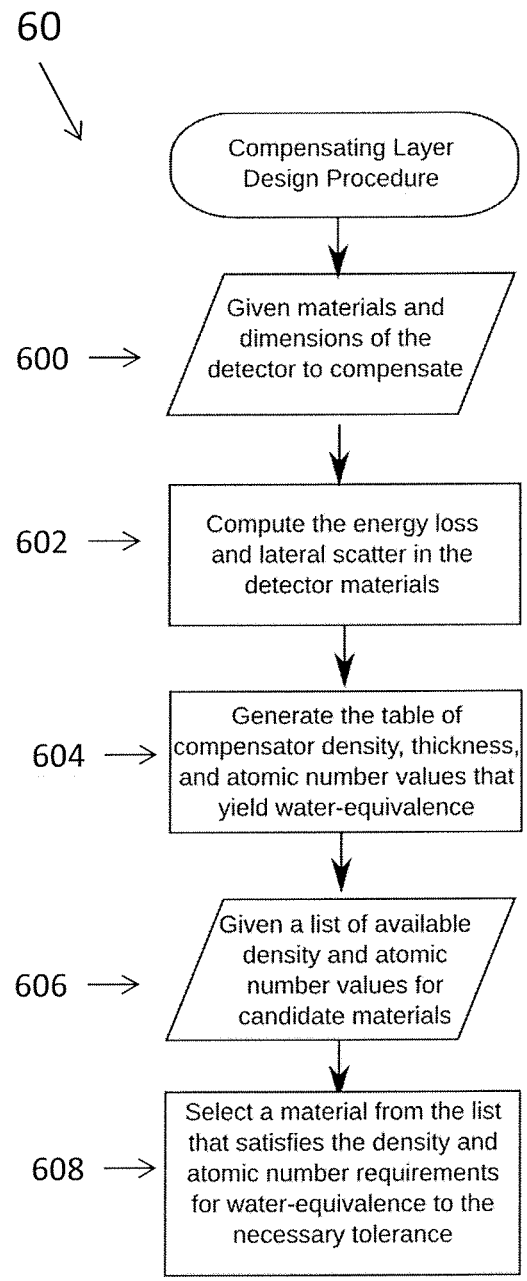
FIG. 6 is a flowchart of steps for designing compensation layers according to aspects of the invention.

At FIG. 6, a flowchart 60 of steps for determining the material for a compensating layer and designing a compensating layer is shown. At block 600, the materials and dimensions of the detector to compensate are given. For clinical use, two dimensional detector arrays will typically have transverse dimensions of at least about 10 cm×10 cm, ideally at least about 25 cm×25 cm. The detector total thickness may be about 1 mm or less for gas-based chambers, thinner for scintillator-based or film-based detectors, down to about 100 microns for semiconductor layers. At block 602, the energy loss and lateral scatter of the radiation beam in the detector materials are computed. At block 604, a table of the compensator density, thickness, and atomic number values that yield water equivalence is generated. At block 606, a list of available density and atomic number values for candidate materials is given. At block 608, a material from the list that satisfies the density and atomic number requirements for water-equivalence to the necessary tolerance is selected. For gaseous detectors, a compensating material of high density may be utilized to compensate the gas with minimal additional thickness. Graphite and boron carbide are examples of materials specific to the Micromegas-based embodiment, though polymers, waxes, and some oxides may be favorable for detectors comprised of different materials and/or different dimensions. Semiconductors are more dense than water so for that class of detectors, compensating layers may be, for example, foams or gasses, even adjacent air layers established by mounting detectors in an air-filled enclosure. In any case, the compensating layer is mounted rigidly to the detector using e.g. fasteners or adhesive. The compensator could be removable to still permit standalone use of the detector in case water-equivalence is not required. The above steps to the method of flowchart 60 disclosed herein are described in detail below.

A design procedure for a two-dimensional detector array is introduced whereby the proton energy loss and scatter are adjusted so that the downstream dose distribution is maintained to be equivalent to that which occurs in uniform water. Starting with the design for an existing, functional two-dimensional detector array prototype, a compensating material is introduced downstream of the detector to simultaneously equate the energy loss and lateral scatter in the detector assembly to water-equivalent values. An analytic formalism and procedure is demonstrated to calculate the properties of the compensating material in the general case of multiple layers of arbitrary material. The resulting design is validated with Monte Carlo simulations. With respect to the specific prototype design considered, the results indicate that a graphite compensating layer of the proper dimensions can yield proton beam range perturbation less than 0.1 mm and beam sigma perturbation less than 2% across the energy range of therapeutic proton beams.

Devices to measure an entire treatment field with full three-dimensional resolution are not commercially available. Some research prototype systems exist, including arrays of ionization chambers, liquid scintillator, plastic scintillator, and amorphous silicon. Another approach is the use of stacks of film or polymer gel, though these require care in handling, time to develop, are not re-usable, have limited dynamic range, and offer no time resolution.

Although a three-dimensional measurement would be ideal, there are commercial devices that provide transverse two-dimensional resolution suitable for proton therapy measurements. Using one of these devices, QA of a patient field is typically performed by collecting multiple 2D measurements at different depths in a water phantom. However, these two-dimensional devices perturb the treatment field to the extent that one array cannot be placed downstream of another. Therefore, it is required that the entire treatment field be delivered multiple times, with the measuring device positioned at a different depth during each delivery. The total setup and delivery time for such a series of QA measurements could be reduced significantly if it were possible to instead deliver each treatment field only once to a phantom containing multiple measuring devices, one positioned at each of the measurement depths.

A possible solution is to define a verification phantom in the treatment planning system (TPS) that includes the measuring devices. However, even if a phantom can be prepared such that the TPS dose calculation algorithm accurately reproduces the proton stopping and scattering within the detector, it would be necessary to setup a phantom for each treatment field because the depths of the detector planes are chosen based on field parameters such as range and modulation. We would have only succeeded in trading the time-consuming in-room QA task for the out-of-room, but still time-consuming, process that is the creation of the model phantom and the dose calculation in the TPS.

A more attractive approach would be to design the detectors to be water-equivalent. In this context, water-equivalent must mean not only that the energy lost by protons in the detector array be equal to the loss if the detector were replaced with water, but also that the amount of multiple Coulomb scattering of protons by the array materials be equal to the scattering that would occur in water. Were this goal achieved, it would be possible to interleave multiple detectors in a solid water-equivalent stack to obtain, in parallel, multiple field profiles that could be compared against the usual TPS dose verification calculated to uniform water.

Figure 7:
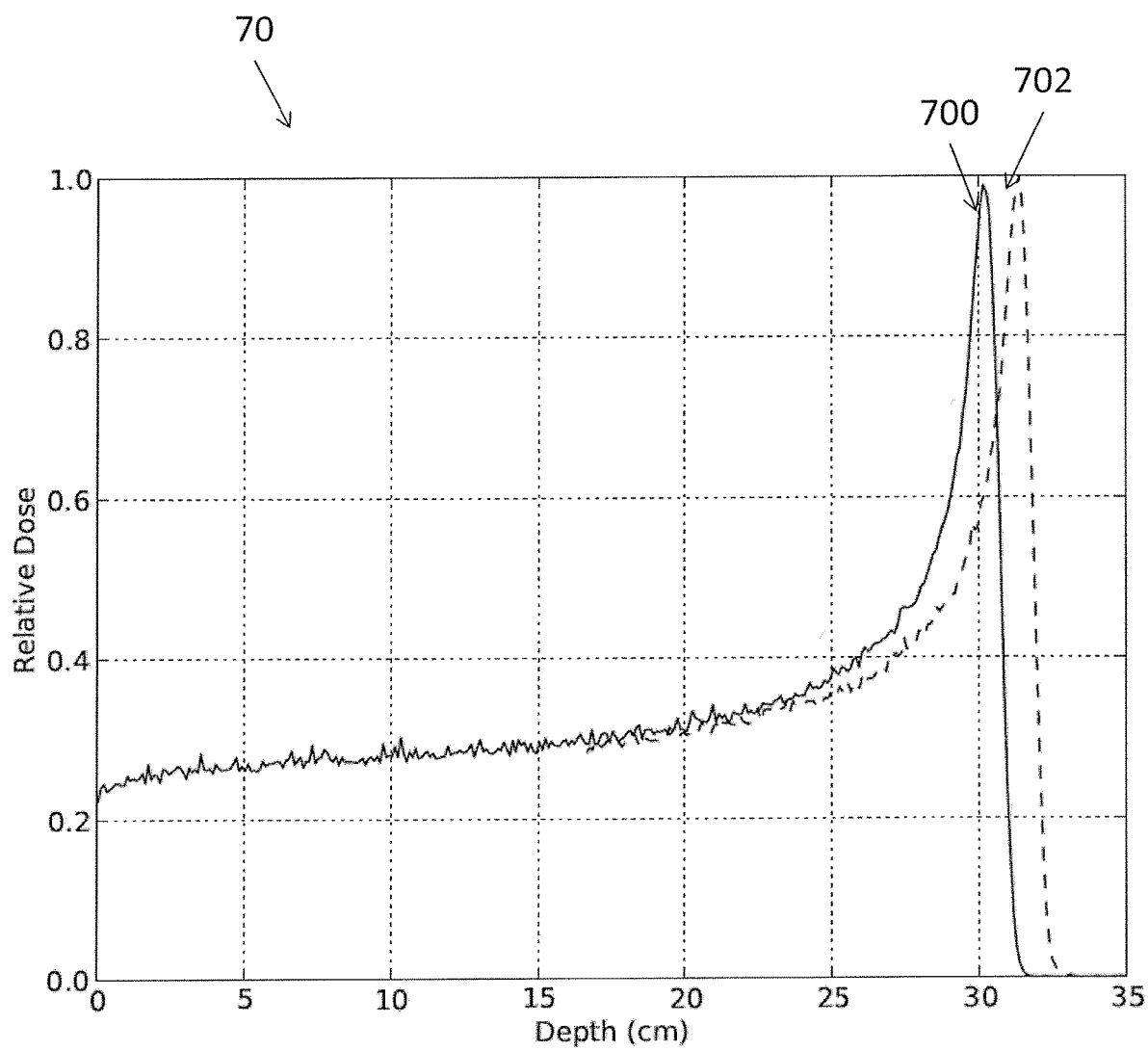
FIG. 7 is a graph depicting dose versus depth range error according to aspects of the invention.
Figure 8:
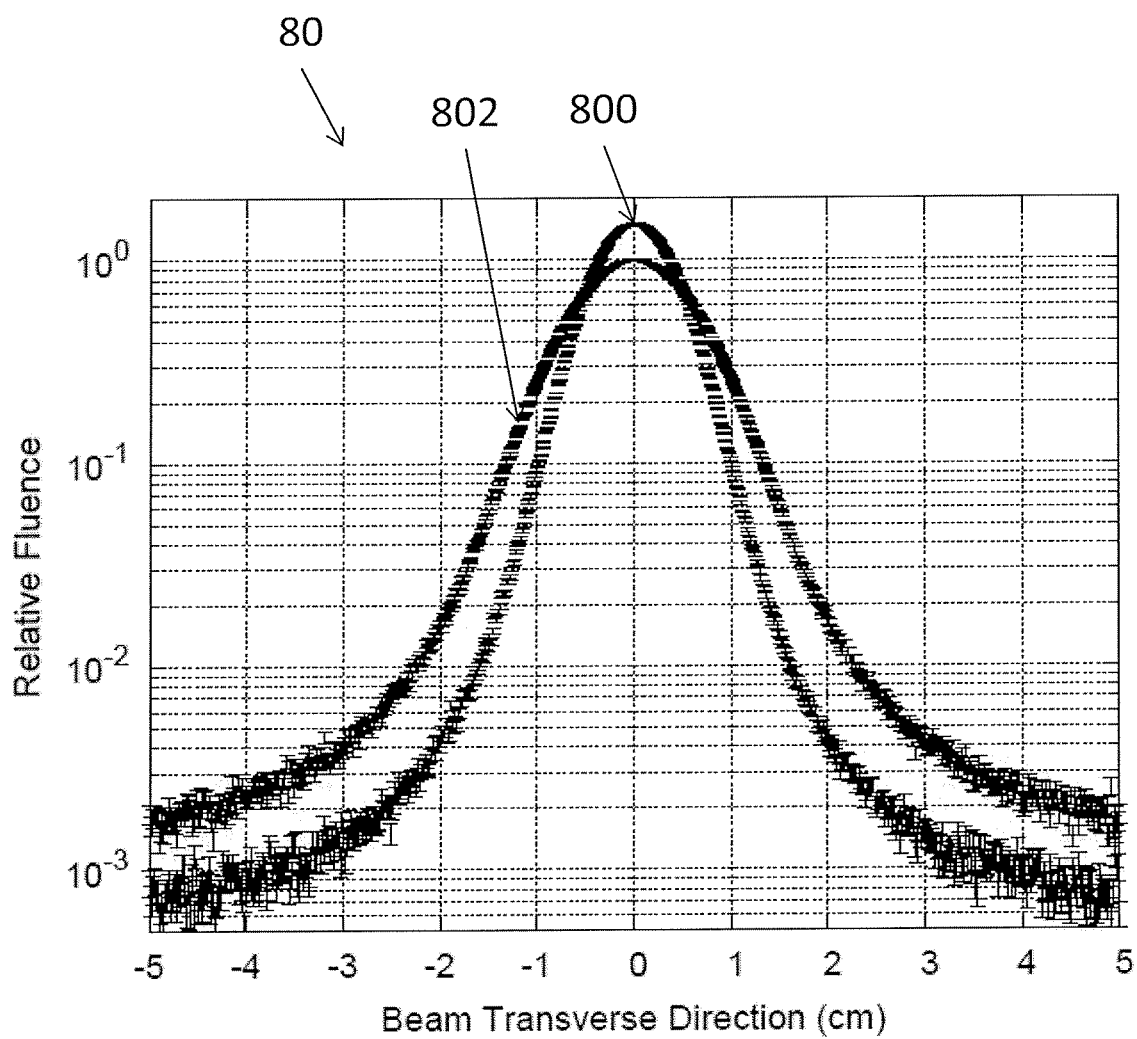
FIG. 8 is a graph depicting lateral profiles of beams according to aspects of the invention.

The inventors have designed, built, and tested a novel two-dimensional detector array. We consider here the perturbation to the beam caused by the detector materials, and explore the feasibility of tuning the energy loss and lateral scatter by adding additional materials to the detector assembly. To make clear the problem at hand, FIG. 7 demonstrates a range perturbation caused by the gas-filled detector array prototype, and FIG. 8 demonstrates the perturbation to the lateral profile. FIG. 7 depicts a graph 70 of a Monte Carlo calculation of the range error downstream of the gas-filled detector prototype with a beam energy of 220 MeV. The solid line 700 is the unperturbed longitudinal dose profile in a water phantom. The dashed line 702 is the dose profile obtained with the detector in a water phantom positioned at the surface. The range error is $\Delta R_{80}=1.1$ cm. FIG. 8 depicts a graph 80 of Monte Carlo calculations of the beam lateral profiles 30 cm downstream of the detector prototype and of a water slab of equal physical thickness for a 100 MeV proton beam. Because the detector is gas-filled, the profile 800 downstream of the detector is more narrow than the profile 802 downstream of water. The beam sigma perturbation is $\Delta\sigma=-30\%$. Due to the gas in the detector, the range difference is greater than 1 cm (relative to water) and the beam spot size downstream of the detector differs by 30%. Certainly a range error of this magnitude would be unacceptable for clinical measurements. A recent publication suggests that, in the context of scanned-beam proton therapy, variation in the spot size of more than 10% results in an unacceptable loss of dose coverage to the clinical target volume (CTV), and therefore, the clinical QA protocol should be designed to be sensitive to spot size differences at this level. The goal for this work was to achieve less than 1 mm range perturbation and less than 10% sigma perturbation relative to uniform water.

The stopping power (in units of MeV $cm^2$ $g^{-1}$) of charged particles heavier than electrons is well described by the Bethe equation:

$$-\left\langle \frac{dE}{dx} \right\rangle = Kz^2 \frac{Z}{A} \frac{1}{\beta^2} \left[ \frac{1}{2} \ln \frac{2m_e c^2 \beta^2 \gamma^2 T_{max}}{I^2} - \beta^2 - \frac{\delta(\beta\gamma)}{2} \right], \quad (1)$$

where Z is the atomic number of the medium, A is its atomic mass, $\rho$ is its density, I is its mean excitation energy, z is the projectile particle charge number, c is the speed of light, $\beta c$ is the velocity of the projectile, $\gamma$ is the Lorentz factor, and $4\pi N_A r_e^2 \, m_e c^2 \approx 0.307$ MeV $cm^2$ $mol^{-1}$ is a constant. $T_{max}$ is the maximum kinetic energy that can be imparted to a free electron in a single collision. At therapeutic proton beam energies, where the proton kinetic energy $T \leq 500$ MeV, the approximation $T_{max} \approx 2 m_e c^2 \beta^2 \gamma^2$ is good to better than 0.2%. Furthermore, the density effect correction, $\delta(\beta\gamma)$ is negligible at such energies. Therefore, for therapeutic proton beams, one may use:

$$-\left\langle \frac{dE}{dx} \right\rangle = K \frac{Z}{A} \frac{1}{\beta^2} \left[ \ln \frac{2m_e c^2 \beta^2 \gamma^2}{I} - \beta^2 \right] \quad (2)$$

$$= K \frac{Z}{A} \left\{ \frac{(T+Mc^2)^2}{T(T+2Mc^2)} \ln \left[ \frac{m_e c^2}{I} \frac{2T(T+2Mc^2)}{(Mc^2)^2} \right] - 1 \right\},$$

where T is the beam kinetic energy and M is the mass of the proton.

We compute the stopping power for a compound with elemental mass fractions as $$\left\langle \frac{dE}{dx} \right\rangle = \sum_i w_i \left\langle \frac{dE}{dx} \right\rangle_i, \tag{3}$$

where $\langle dE/d\chi \rangle_i$ is the stopping power for the i-th element. Finally, we approximate the total energy lost in a stack of multiple material layers as $$E_{loss} = \sum_l t_l \rho_l \left\langle \frac{dE}{dx} \right\rangle_l, \tag{4}$$

where the $t_l$ and $\rho_l$ represent the thickness and density of layer l. Note that this is essentially a thin-layer approximation, because it ignores the energy lost in previous layers to compute the per-layer stopping powers.

In thick material layers, the energy loss as a function of material thickness can be accurately determined by the use of an inverse range table.

When a charged particle passes through a medium, it is deflected by many Coulomb scattering interactions with nuclei. To estimate the width, $\theta_0$, of the projected angular distribution of protons due to multiple Coulomb scattering (MCS), we use the fit of Lynch & Dahl, $$\theta_0 = \frac{13.6 \text{ MeV}}{\beta c p} z \sqrt{\frac{x}{X_0}} \left( 1 + 0.038 \ln \frac{x}{X_0} \right), \tag{5}$$

for protons of momentum $\rho$ and velocity $\beta c$. The quantity $x/X_0$ represents the thickness of the scattering medium in units of the radiation length, which is calculated using a formula computed by Tsai (1974).

$$\frac{1}{X_0} = 4\alpha r_e^2 \frac{N_a}{A} \{Z^2[L_{rad}(Z) - f(Z)] + ZL'_{rad}(Z)\}, \tag{6}$$

and making use of the rational function approximation of Davies for the infinite sum f(Z). The dependence on Z is somewhat obscured in this formula; we merely point out for the benefit of the reader that a fit function makes more apparent the dependence of $X_0$ on Z and Z=A and agrees with Tsai's values to better than 2.5%:

$$X_0 \approx \frac{716.4 \text{ g cm}^{-2} A}{Z(Z+1)\ln(287/\sqrt{Z})}. \tag{7}$$

The radiation length in a mixture or a compound is calculated as $$1/X_0 = \sum_i w_i/X_i. \tag{8}$$

Note that the relative difference in $\theta_0$ between two different scattering layers will be independent of energy, at least in the context of multiple Coulomb scattering where Equation 5 is a good approximation.

A simplified model of a 2D detector array is used. The detector is essentially a parallel-plate detector with a gaseous ionization volume between two electrodes etched in copper on printed circuit boards (PCBs). The PCBs are G10 standard board material of 1.5 mm (anode) and 1.8 mm (cathode) thicknesses. The electrodes are spaced 1.3 cm apart, and the fill gas is 70% Argon and 30% CO2. This model includes the most significant components that influence the stopping and scattering of primary protons. For simplicity, we neglect materials that are expected to cause only minor additional perturbations to the stopping or scattering, such as the thin copper traces on the PCB. Nevertheless, our method is general and can accommodate any number of materials.

Figure 9:
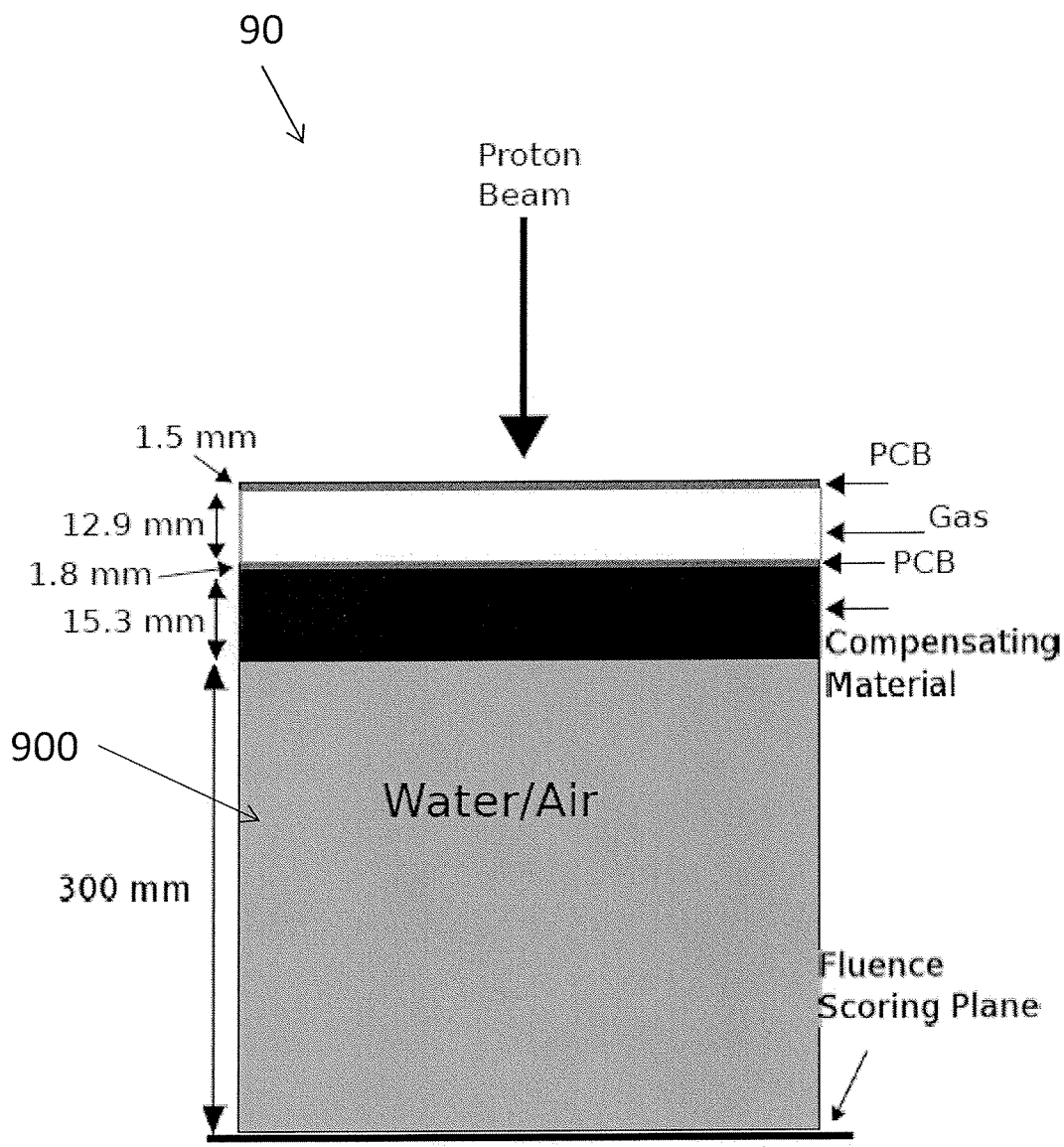
FIG. 9 is a diagram of a detector system in accordance with aspects of the invention.

FIG. 9 shows a schematic of suitable detector components plus an additional compensating material to be discussed further below. To obtain the water-equivalent thickness of the detector assembly, longitudinal dose profiles are scored in the water-filled phantom 900 positioned downstream of the detector assembly 90. Beam lateral profiles downstream of the detector assembly were recorded, using the air filled phantom, on the fluence scoring plane which was placed 30 cm downstream of the detector to represent the worst-case scenario in terms of perturbation to the beam spot properties relative to water. The water phantom shown in FIG. 9 is relevant for the Monte Carlo simulations. The physical properties for each material in a suitable detector assembly are listed in Table 1.

TABLE 1

Detector Material Properties. The $\langle I \rangle$ and $\langle Z/A \rangle$ values given here for compounds and mixtures were calculated using the appropriate weighting determined by substituting Equation 1 into Equation 3, while $\langle Z \rangle$ was determined by first calculating the radiation length using Equation 8 and inverting Equation 6. Energy loss values were calculated using Equation 4. $X_0$ was determined using Equation 6.

| Material | $\rho$ (g cm$^{-3}$) | $\langle Z/A \rangle$ (g$^{-1}$ mol) | $\langle I \rangle$ (eV) | $\langle Z \rangle$ | t (mm) | $E_{loss, 230 MeV}$ (MeV) | $E_{loss, 100 MeV}$ (MeV) | $x/X_0$ |
|---|---|---|---|---|---|---|---|---|
| Top PCB | 1.70 | 0.53 | 88.3 | 8.8 | 1.5 | 0.999 | 1.767 | 0.0086 |
| Ar/CO$_2$ (1 atm) | 0.00170 | 0.47 | 156.5 | 14.2 | 12.9 | 0.007 | 0.012 | 0.00009 |
| Bottom PCB | 1.70 | 0.53 | 88.3 | 8.8 | 1.8 | 1.165 | 2.061 | 0.010 |
| Graphite | 1.9 | 0.50 | 78.0 | 6.0 | 15.3 | 10.727 | 19.015 | 0.068 |
| Water | 1.00 | 0.56 | 78.0 | 7.9 | 31.5 | 12.897 | 22.855 | 0.087 |

In general, the stack of materials that comprise the detector will not be water-equivalent neither with respect to energy loss nor to the scattering of traversing protons. We introduce a compensating material downstream of the detector and set out to determine the material properties and the thickness for this layer such that the overall assembly be water-equivalent.

Concerning the design of our particular detector, the water-equivalent thickness (WET) is less than the same physical thickness of water, due to the relatively thick gas volume. Therefore, we need a material with density greater than water to compensate. Given a material, the thickness of the compensating material is determined such that the energy loss in the detector plus compensator assembly, as calculated using Equation 4, is equal to the energy lost within a slab of water of thickness $$t_W = t_{PCB} + t_{gas} + t_c \tag{9}$$

The subscript w denotes water, and c denotes compensating material. This equation is specific to the model detector, however the general case would just replace the right hand side with $$\Sigma_i t_i.$$

Equation 5 is a fit for the scattering angle as a function of scatterer thickness in units of radiation length. To apply that equation to a multi-layer system we calculate $x/X_0$ for the combined scatterer system as the sum $$\frac{x}{X_0} = \sum_l \frac{x_l}{X_{0,l}}. \tag{10}$$

Equation 5 represents a fit to experimental data obtained with relatively thin target material slabs. Equation 5 is accurate to 11% or better for $10^{-3} \leq x/X_0 \leq 100$. The thin layer approximations are appropriate for radiologically-thin detector assemblies such as Micromegas constructed using aluminized Mylar or polyimide-based electrodes.

Figure 10A:
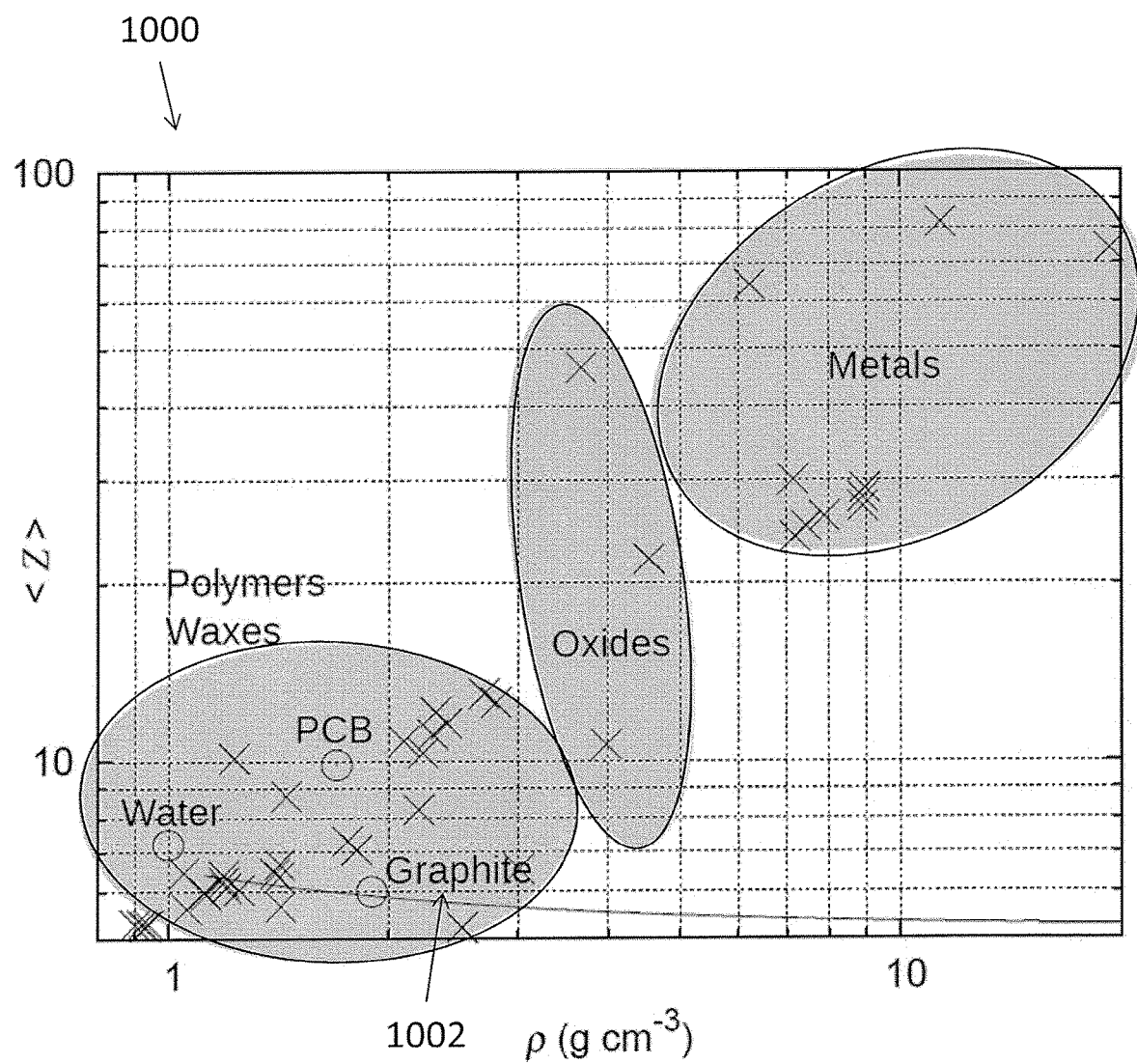
FIGS. 10A and 10B are plots depicting various materials tested for use in compensation layers according to aspects of the invention.

FIG. 10A is a plot 1000 of effective (mass fraction-weighted) atomic number versus density for some materials. The points indicate the density and atomic number for real materials. The solid line 1002 represents an ideal density and atomic number values for which there exists a slab thickness that balances the energy loss (Equation 9) and multiple-scattering (Equation 10) with water of the same physical thickness as the detector plus compensating layer thickness. The line 1002 represents the ideal atomic number versus material density. This line was obtained by computing, given the density, the thickness required to compensate energy loss using Equation 9. For this calculation, we used Z/A=0.5 and the water value I=78 eV. We then determine the ideal radiation length for the material, given the density and calculated thickness values, using Equations 5 and 10. This ideal radiation length is used to determine the ideal Z using Equation 6. This procedure generates a relation Z(ρ) which represents, up to the approximations discussed above, a density and effective atomic number pair for a compensating material such that the energy lost and the amount of Coulomb scattering in the detector plus compensating material is the same as in a slab water of the same physical thickness. That is, the detector plus compensator assembly is water-equivalent in both senses.

As shown in FIG. 10A, graphite is a material that lies very close to the line and has relatively high density. Materials with greater density tend to also have atomic number above the ideal curve. Graphite has the additional advantage that it can be pressed into sheets at relatively low cost. We use the density value of 1.9 g/cm3 for graphite since this is typical for high-purity isostatic graphite.

As disclosed herein, more accurate thick-slab calculation, which includes the effects of proton energy loss and effective scattering origin within a slab, determines that for certain classes of detector assemblies, for example those using printed circuit board (PCB) based electrodes, various glasses and aluminum oxide make excellent compensating materials. Furthermore, the PCB material itself provides a nearly ideal ρ, Z, combination such that, by appropriate balance of PCB thickness against the other constituent materials, detectors can be designed to be effectively self-compensating.

For thicker material slabs, the total scattering angle is more accurately computed by integrating Equation 5 over the slab thickness, t:

$$\theta_0 = K_1 z \left(1 + K_2 \ln \frac{x}{X_0}\right) \left[\int_0^t \left(\frac{1}{\beta c p}\right)^2 \frac{dx}{X_0}\right]^{1/2} \tag{11}$$

Note that energy loss is accounted for in the integrand since β and ρ are functions of the proton kinetic energy, which can be accomplished by the use of an inverse range table as described above.

This scattering angle calculation is fit to experimental data via the coefficients $K_1$ and $K_2$. The integral form for $\theta_0$ is suitable for assemblies containing one or more thick material slabs, such as the standard G10/FR4 printed circuit boards that include the electrodes of the prototype Micromegas assembly described in Table 1 above. In the multi-layer case, a sum of integrals over each slab is performed, such that the energy loss within each slab is properly accounted (via β and ρ in equation (11) above).

Figure 10B:
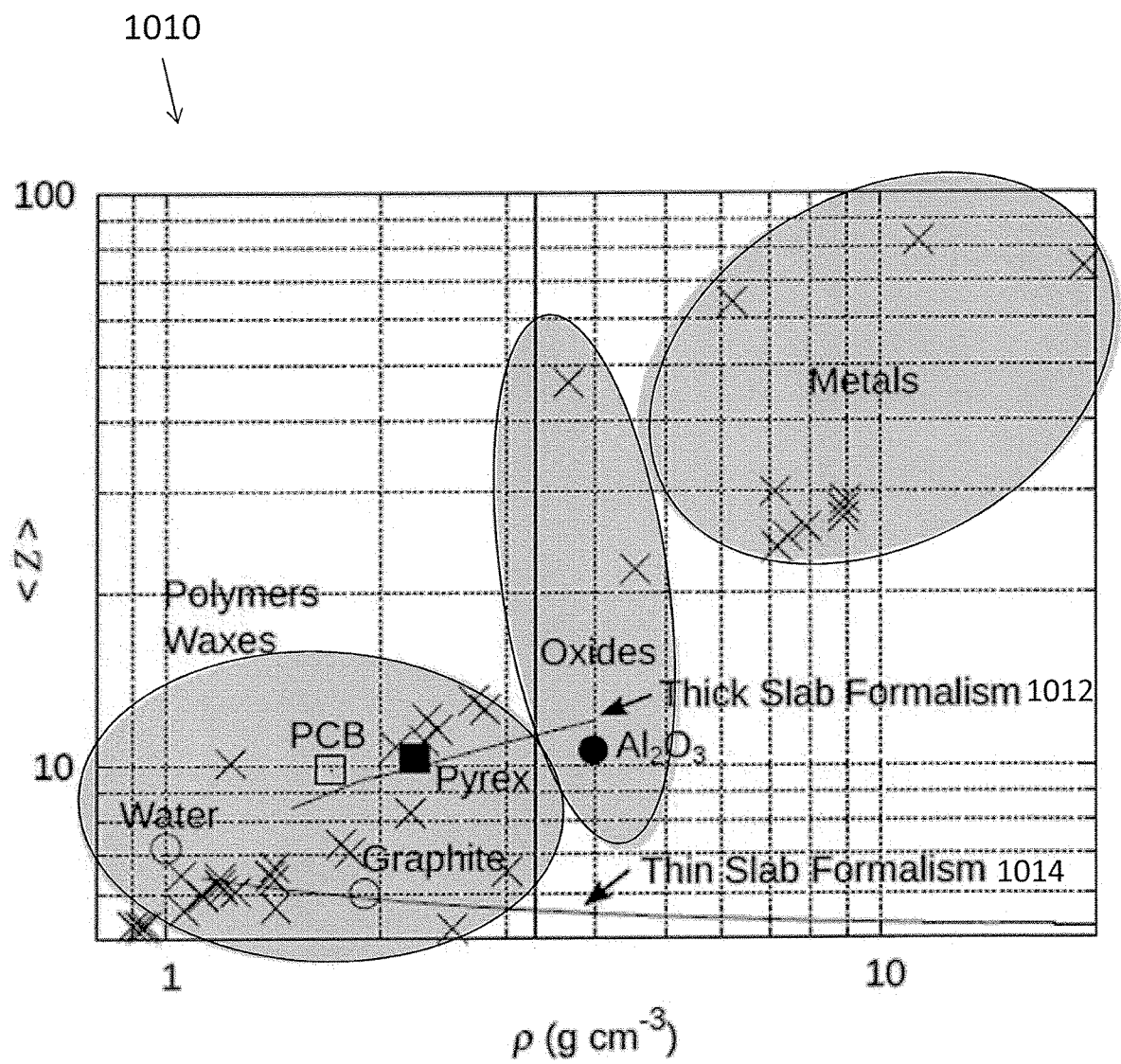

For detector assemblies that include relatively thick material slabs, the more appropriate thick-target formulae described above better determine ideal compensating material density and atomic number combinations. FIG. 10B is a plot 1010 of effective (mass fraction-weighted) atomic number versus density for relatively thick slab materials and thin materials. In FIG. 10B, the upper line 1012 represents ideal density and atomic number values computed using the thick target formulism. The lower line 1014 represents the ideal material properties as computed using the thin target formulism. The upper line 1012 is expected to be more accurate in case the detector electrodes are fabricated on standard G10/FR4 printed circuit boards.

Referring to FIG. 10B, atomic number versus density for determining properties of compensating materials is shown. The points (e.g., the "X"s) indicate the density and atomic number for real materials. The solid lines (e.g., lines 1012 and 1014) represent ideal density and atomic number values for which there exists a slab thickness that balances the energy loss (equation (9)) and multiple scattering (equation (10)) with water of the same physical thickness as the detector plus compensating layer thickness. The lower line 1014 was computed using the thin layer approximations, while the upper line 1012 represents the more accurate thick layer formalism.

The linear stopping power, that is $\rho \times \langle dE/d\chi \rangle$, is primarily a function of density. Some dependence on Z enters as Z/A, though that is typically ≈0.5, and via the mean excitation energy. The mean excitation energy I≈10Z, and enters the stopping power as ln I. So the stopping power dependence on Z is relatively weak, compared with the scattering angle dependence which is √Z to lowest order. What we have managed to show is that we can use the material density and layer thickness to tune the energy loss within a detector system, and that we can use Z to simultaneously tune the amount of multiple Coulomb scattering, in order to achieve water-equivalence with respect to these two important beam propagation characteristics.

To be more quantitative, one should consider the sensitivities of proton stopping and scattering to the material properties $\rho$, Z, and I. Since the energy loss is linear in material density, the goal to keep range error less than 1 mm imposes a stringent requirement on the material density. A mere 3.5% variation in the compensating material density is enough to modify the range by more than 1 mm, given that our slab thickness is 1.5 cm. With respect to proton scattering, the effect of density variation is weaker, scaling rather as $\sqrt{\rho}$, and we suppose to accept 10% sigma deviation. The fact that the range requirements are more stringent is a consequence of the fact that the dose gradient in the beam longitudinal direction is greater than the lateral gradient (penumbra). There are two distinct issues: one of design and one of manufacture. Our design procedure overcomes the sensitivity to density by choice of the compensating layer thickness. In manufacture, the sensitivity to density must translate to a tight tolerance on the density variation between compensating layers.

By contrast, the detector WET is not so sensitive to the I value. It would need to differ from the nominal graphite value by more than 20 eV (26%) to produce a 1 mm WET error, which would require <Z> <4 (Be) or <Z>>8 (O). The atomic number should be kept between $4 \leq Z \leq 7$ in order that the $\sigma$ variation be below the 10% threshold. The fact that the Z-dependencies of the energy loss and scattering are somewhat weak, and the scattering error tolerance somewhat large, means that there is some forgiveness in the choice of compensating material, and some tolerance to impurities in the manufactured product. For example, it may be possible to find a lower cost material, with high density, but <Z> a few numbers away from the ideal value, that would give acceptable results.

In estimating the detector WET and the beam sigma downstream of the detector, errors occur due to the approximations described above. With respect to the scattering calculation, Equation 5, the energy loss in the detector is ignored, and furthermore Equation 8 treats the multi-layer detector as if all of the materials in the layers were distributed uniformly over the physical thickness of the assembly.

Since in the detector assembly, there is underdense (relative to water) gas upstream of overdense graphite, the effective scattering source position is shifted somewhat towards the exit face of the detector, relative to the source position in uniform water. The reason that the scattering difference is worse at lower energies is that the energy loss within the detector layers is greater at lower energies and the difference in the effective source position between the detector and uniform water becomes larger. In spite of this systematic error, if the tolerance on spot size perturbation is really 10% or higher, then we have indeed shown here that our approximations are justified and that errors are kept below the threshold for clinical relevance.

By default, without a user-entered step limitation, Geant4 limits the step size in a material to 20% of the particle range in the material. The result is that there is typically one step in graphite for beam energies greater than 138 MeV, but two steps in water up to 150 MeV. The MCS process is non-linear and so there is a discontinuity between the one-step and two-step MCS calculations. The relative difference in the beam sigma between the 1- and 2-step calculations is about 0.8% and corresponds to the difference observed in this energy range. We observe no difference in our beam sigma ratios between simulations using 2 and 5 steps in the layers.

It is important to reinforce that the errors discussed here in the range and in the scattering angle for the detector relative to water are systematic. In the case of a multi-layer system, it must be considered that the errors from each imperfectly-compensated layer will accumulate. The range error we have achieved is 0.2 mm, meaning that about 5 layers could be used before the accumulated range error exceeds our clinical tolerance of 1 mm. A less than 2% error in scattering was achieved, which also suggests that we could stack about 5 layers.

A compensating material with high density was favored because the thickness of the compensating material imposes a limitation on how closely the active layers can be stacked in a multi-layer, water-equivalent system. Materials with density greater than the selected graphite tend to have atomic numbers that are too large to correctly compensate the proton scattering. However, since it is thought that 10% scattering error is tolerable, it may be possible to find a higher density compensator such that the layer would be physically thinner and yet the scattering be within tolerance. We have also considered a multi-layer compensation solution, though the fact that the Z requirement is not very stringent suggests that a one-material solution can probably be found for most detector geometries.

A thorough analysis of perturbations to the measured dose downstream of the detector must also consider the modification of the spectrum of secondary particles by the detector elements relative to water, due to different interaction cross-section for protons in the materials. The fluence correction factor to the absolute dose measured in graphite relative to that measured in water is reported to be as high as 4% for 200 MeV protons. The size of the effect may be mitigated somewhat by the reduced thickness of the compensating layer, as compared with the beam range, however the effect of the graphite as well as the other layers comprising the detector should be investigated since it could present a challenge for the calibration of a multi-layer compensated system because corrections for the modification of secondary particle spectra will be energy dependent.

Figure 11:
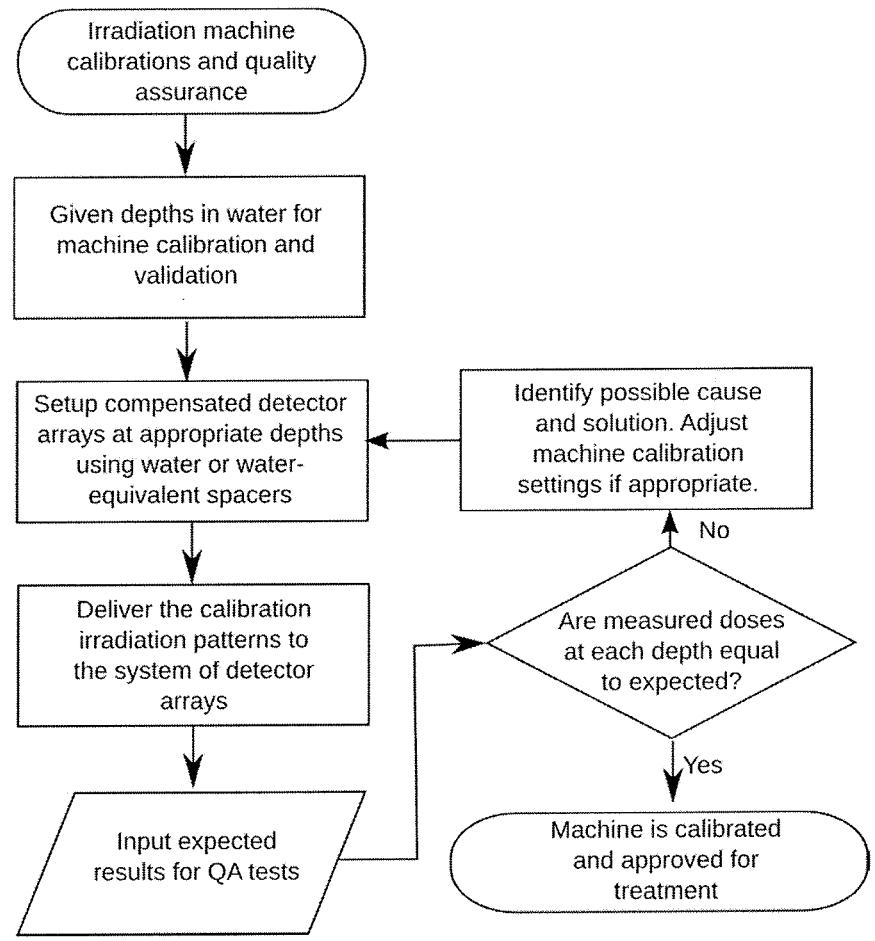
FIG. 11 is a flowchart depicting steps for calibrating irradiation machines according to aspects of the invention.

At FIG. 11, a flowchart of steps for calibration and quality assurance of an irradiation machine is shown. Depths in water for machine calibration and validation are given. Then, compensated detector arrays in accordance with aspects of the invention are set up at appropriate depths using water or water-equivalent spacers. The calibration irradiation patterns to the system of detector arrays are delivered, and expected results for the quality assurance tests are inputted. Usual methods for two-dimensional or three-dimensional dose comparisons are employed at this step such as gamma analysis or distance-to-agreement (DTA). If the measured doses at each depth are judged not to equal expected results within clinical tolerance, the possible cause and solution are identified and the calibration settings are adjusted if appropriate. If the measured doses at each depth do equal the expected results, the machine is calibrated and approved for treatment.

Figure 12:
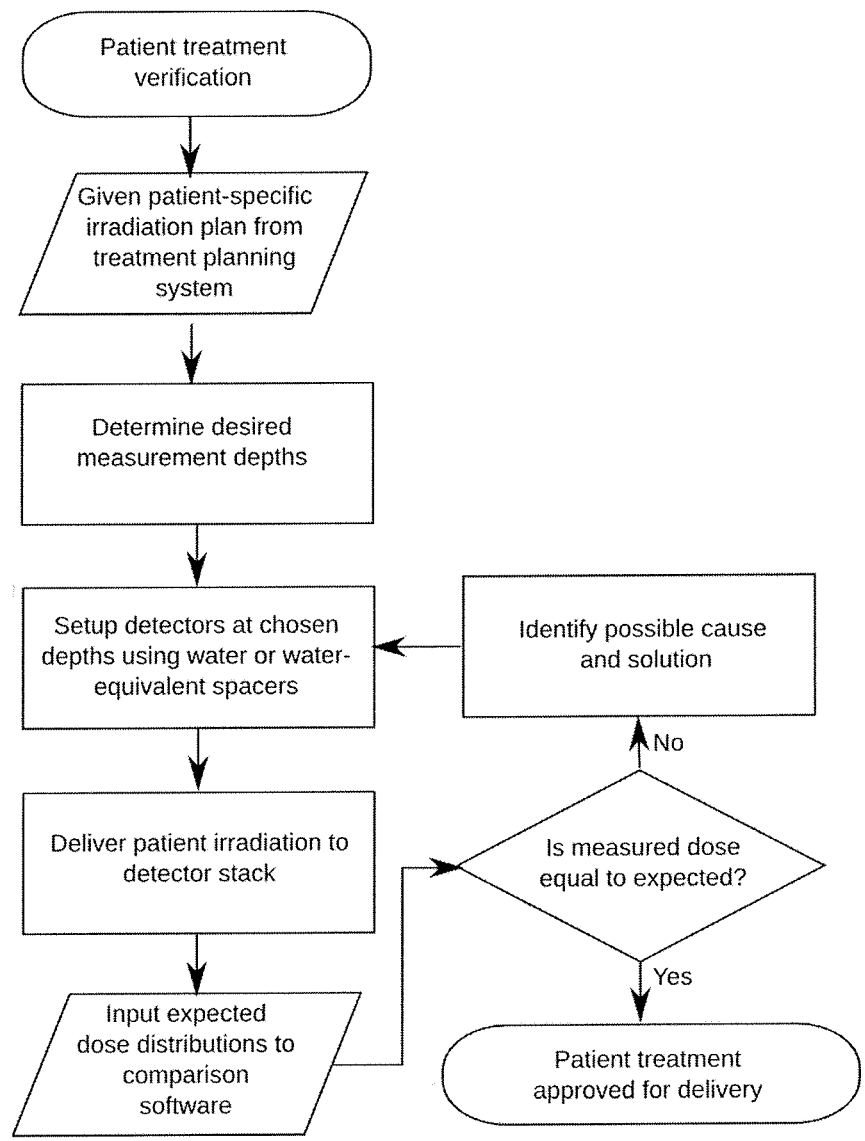
FIG. 12 is a flowchart depicting steps for verifying patient treatment according to aspects of the invention.

At FIG. 12, a flowchart of steps for patient treatment verification is depicted. A patient specific irradiation plan from a treatment planning system are given and desired measurement depths are determined. Detectors in accordance with aspects of the invention are set up at chosen depths using water or water equivalent spacers, and the patient irradiation is delivered to the detector stack. Expected dose distributions are inputted to comparison software that performs gamma analysis, distance-to-agreement (DTA), or other accepted 2D or 3D dose comparison method. If the measured does is not equal to the expected dose within clinical tolerance, the possible cause and solution are identified. If the measured dose matches the expected dose, the patient treatment is approved for delivery.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A particle detection device, comprising:
    a plurality of particle detection layers configured to detect, at respective locations of the plurality of particle detection layers, a two-dimensional spatial profile of a particle beam transverse to a direction of travel of the particle beam; and
    one or more compensation layers configured to adjust energy loss and scattering transverse to the direction of travel introduced by the plurality of particle detection layers to match water-equivalent values for scattering transverse to the direction of travel, each compensation layer positioned adjacent a respective one of the plurality of particle detection layers.

2. The device of claim 1, wherein at least one layer of the plurality of particle detection layers is a parallel-plate detector configured to measure the two-dimensional spatial profile of the particle beam transverse to the direction of travel of the particle beam.

3. The device of claim 2, wherein at least one of the parallel-plate detectors is a Micromegas detector.

4. The device of claim 1, wherein each of the one or more compensation layers comprises a layer of graphite.

5. The device of claim 1, wherein the plurality of particle detection layers comprises at least three stacked particle detection layers, wherein each of the at least three stacked particle detection layers is configured to separately measure the two-dimensional spatial profile of the particle beam transverse to the direction of travel of the particle beam.

6. The device of claim 1, wherein the plurality of particle detection layers comprises at least five stacked particle detection layers, wherein each of the at least five stacked particle detection layers is configured to separately measure the two-dimensional spatial profile of the particle beam transverse to the direction of travel of the particle beam.

7. The device of claim 1, wherein space between each of the plurality of particle detection layers and respective compensation layers is filled with water or a water-equivalent material.

8. The device of claim 1, wherein the distance between a first of the plurality of particle detection layers positioned upstream and a second of the plurality of particle detection layers positioned downstream is between 300 mm and 350 mm.

9. The device of claim 1, wherein the particle detection device is configured for the detection of protons as the particle.

10. The device of claim 1, further comprising an additional compensation layer mounted to the one or more compensation layers and being positioned adjacent to the one or more compensation layers.

11. The device of claim 1, wherein the one or more compensation layers comprise at least one of a foam or gas.

12. The device of claim 11, wherein the one or more compensation layers are mounted to the plurality of particle detection layers in an air-filled enclosure.

13. The device of claim 1, wherein the one or more compensation layers are removable from the plurality of particle detection layers.

14. The device of claim 1, wherein the plurality of particle detection layers comprise at least one semiconductor layer configured to measure the two-dimensional spatial profile of the particle beam transverse to the direction of travel of the particle beam.

15. A method for calibrating a particle therapy machine, the method comprising:
    directing a particle beam in accordance with a calibration plan into a particle detection device, wherein the particle detection device comprises:
        a plurality of particle detection layers configured to detect, at respective locations of the plurality of particle detection layers, a two-dimensional spatial profile of the particle beam transverse to a direction of travel of the particle beam; and
        one or more compensation layers configured to adjust energy loss and scattering transverse to the direction of travel introduced by the plurality of particle detection layers to match water-equivalent values for scattering transverse to the direction of travel, each compensation layer positioned adjacent a respective one of the plurality of particle detection layers;
    comparing measured energy and direction values from a scoring plane to expected values to determine at least one compensation value; and
    adjusting the particle therapy machine based on the at least one compensation value to calibrate the particle therapy machine.

16. A method for validating a particle therapy plan, the method comprising:
    directing a particle beam in accordance with the particle therapy plan into a particle detection device, wherein the particle detection device comprises:
        a plurality of particle detection layers configured to detect, at respective locations of the plurality of particle detection layers, a two-dimensional spatial profile of the particle beam transverse to a direction of travel of the particle beam; and
        one or more compensation layers configured to adjust energy loss and scattering transverse to the direction of travel introduced by the plurality of particle detection layers to match water-equivalent values for scattering transverse to the direction of travel, each compensation layer positioned adjacent a respective one of the plurality of particle detection layers;
    comparing measured energy and direction values from a scoring plane to expected values to determine at least one discrepancy; and
    validating the particle therapy plan if the at least one discrepancy is within an acceptable range.

17. A method for determining a compensation layer material for use in a particle detection device, the method comprising the steps of:
    computing an energy loss and scatter values based on material information and dimension information of a plurality of particle detection layers in the particle detection device, wherein the scatter values account for scattering transverse to a direction of travel of a particle beam;
    generating values for a density, an atomic number, and a thickness of the compensation layer that in combination with the plurality of particle detection layers yield a water equivalent system; and determining an available material satisfying a combination of the density, atomic number, and thickness values generated for the compensation layer.

18. The method of claim 17, wherein one or more of the energy loss or the scatter values account for interactions in the direction of travel of the particle beam.

* * * * *